United States Patent [19]

Conners

[11] Patent Number: 5,306,283
[45] Date of Patent: Apr. 26, 1994

[54] TWO-PART SURGICAL LIGATION CLIP

[75] Inventor: John A. Conners, Fairfield, Conn.

[73] Assignee: American Cyanamid Company, Wayne, N.J.

[21] Appl. No.: 906,938

[22] Filed: Jun. 30, 1992

[51] Int. Cl.⁵ .............................................. A61B 17/00
[52] U.S. Cl. ..................... 606/151; 606/158; 227/902
[58] Field of Search ............... 606/120, 151, 157, 158; 227/902; 24/328, 337, 492, 498, 517, 518, 520, 527, 528, 537, 545, 555, 563, 568

[56] References Cited

U.S. PATENT DOCUMENTS

| | | | |
|---|---|---|---|
| 1,274,006 | 6/1918 | Clarke et al. | 24/517 |
| 2,583,680 | 1/1952 | Brennan | 24/537 |
| 3,049,782 | 8/1962 | Hawie | 24/537 |
| 3,326,217 | 6/1967 | Kerr | 606/158 |
| 3,882,854 | 5/1975 | Hulka et al. | |
| 3,924,303 | 12/1975 | Elliott | 24/537 |
| 3,932,918 | 1/1976 | Paskert | 24/537 |
| 4,064,881 | 12/1977 | Meredith | |
| 4,169,476 | 10/1979 | Hilterbrandt | |
| 4,505,010 | 3/1985 | Arenhold | 24/568 |
| 4,566,157 | 1/1986 | Packendorf | 24/537 |
| 4,590,937 | 5/1986 | Deniega | |
| 4,788,966 | 12/1988 | Yoon | 128/831 |
| 4,869,268 | 9/1989 | Yoon | 128/831 |
| 4,950,258 | 8/1990 | Kawai et al. | 604/281 |
| 5,100,418 | 3/1992 | Yoon et al. | 606/151 |
| 5,171,253 | 12/1992 | Klieman | 606/158 |
| 5,201,746 | 4/1993 | Shichman | 606/151 |

FOREIGN PATENT DOCUMENTS

| | | |
|---|---|---|
| 0490411 | 6/1993 | European Pat. Off. |
| 2932652 | 2/1981 | Fed. Rep. of Germany ...... 606/151 |
| 1534916 | 6/1968 | France ................ 606/120 |

*Primary Examiner*—Stephen C. Pellegrino
*Assistant Examiner*—J. A. Schmidt

[57] ABSTRACT

A two-part surgical ligation clip includes a track having two substantially symmetrical arms and a clip for slidably receiving the track. The symmetrical arms are connected together at a proximal end to form an apex and have spaced-apart tips at a distal end with first complementary surface. The track also includes a connector connected to the apex and having a second complementary surface. The clip has an extended slot for slidably engaging the track and distal end tips for receiving the connector. A distal end of the clip has a first contour surface for engaging the first complementary surface on the track and locking it in a closed position and a second contour surface for engaging the second complementary surface on the track and locking it in an open position.

30 Claims, 5 Drawing Sheets

TWO-PART SURGICAL LIGATION CLIP

BACKGROUND OF THE INVENTION

1. Field of the Invention

The present invention relates to a surgical ligation clip typically used during a surgical procedure. More particularly, the ligation clip of the present invention provides a two-part assembly comprised of a track for gripping, for example, a blood vessel and a clip for closing the track to ligate the blood vessel.

2. Description of the Prior Art

Ligation clips used in surgical procedures are well known in the art. For example, clips are used in surgical procedures to ligate blood vessels. Typically, a surgical ligation clip uses a clamp to compress a severed blood vessel to stop the flow of blood.

One example of a surgical ligation clip is provided by U.S. Pat. No. 4,590,937, which is assigned to the assignee of the subject application. That surgical clip is formed of two substantially symmetrically-shaped arms connected together at an apex and a U-shaped member for manipulating the arms. Each arm comprises a more flexible portion and a bend at the more flexible portion. The surgical clip is positioned around the blood vessel to be ligated and the arms are manipulated to form a diamond-shaped enclosure around the blood vessel. The apex of the arms is slid within the U-shaped member to collapse the arms at the more flexible portions and tightly compress the blood vessel therebetween. The surgical ligation clip is made from a non-metallic material such as a synthetic bioabsorbable polymer with, for example, a glycolic and ester linkage.

While the clip disclosed in U.S. Pat. No. 4,590,937 incorporates many advantageous features, still further improvements in surgical ligation clips are desirable. For example, the subject invention provides a track with a surface for improved gripping of the blood vessel. In addition, a clip and the track are designed to cooperate with each other to temporarily lock the track in an open position for easy positioning of the clip around the blood vessel and to temporarily lock the track in a closed position for securely compressing the blood vessel. Still further, the clip of the subject invention is provided with tapered ribs to strengthen it and provide a tighter hold on the ligated blood vessel.

SUMMARY OF THE INVENTION

It is an object of the present invention to provide an improved surgical ligation clip.

It is another object of the present invention to provide a surgical ligation clip with a track for better gripping the blood vessel to be ligated.

It is a further object of the present invention to provide a track and a clip which cooperate with each other to lock the track in an open position.

It is still a further object of the present invention to provide a track and a clip which cooperate with each other to lock the track in a closed position.

It is yet another object of the invention to provide a clip with increased strength for tightly securing the blood vessel within the closed track.

In accordance with one aspect of the invention, a two-part surgical ligation clip comprises a track including two substantially symmetrical arms connected together at a proximal end to form an apex and having spaced tips at a distal end with first complementary surfaces. The track also includes a connector connected to the apex and having a second complementary surface. In addition, a clip has an extended slot for slidably engaging the track and distal end tips for receiving the connector. Each distal end tip has a first contour surface for engaging the first complementary surface on the track and locking it in a closed position and a second contour surface for engaging the second complementary surface on the track and locking it in an open position.

In accordance with another aspect of the invention, a surgical ligation clip comprises a track having two arms for engaging around a vessel to be ligated, with the arms being joined together at a proximal end of the track. A clip has an extended slot for slidably receiving the track. In addition, first locking means locks the track in a closed position in the clip, and second locking means locks the track in an open position in the clip.

These and other objects, aspects, features and advantages of the present invention will become apparent from the following detailed description of the preferred embodiments taken in conjunction with the accompanying drawings.

DESCRIPTION OF THE PREFERRED EMBODIMENTS

For convenience of reference, as used herein, the term "distal" will refer to that part of the device which is farthest away from the surgeon-user, and the term "proximal" refers to that part of the device which is closest to the surgeon-user.

Figure 1:
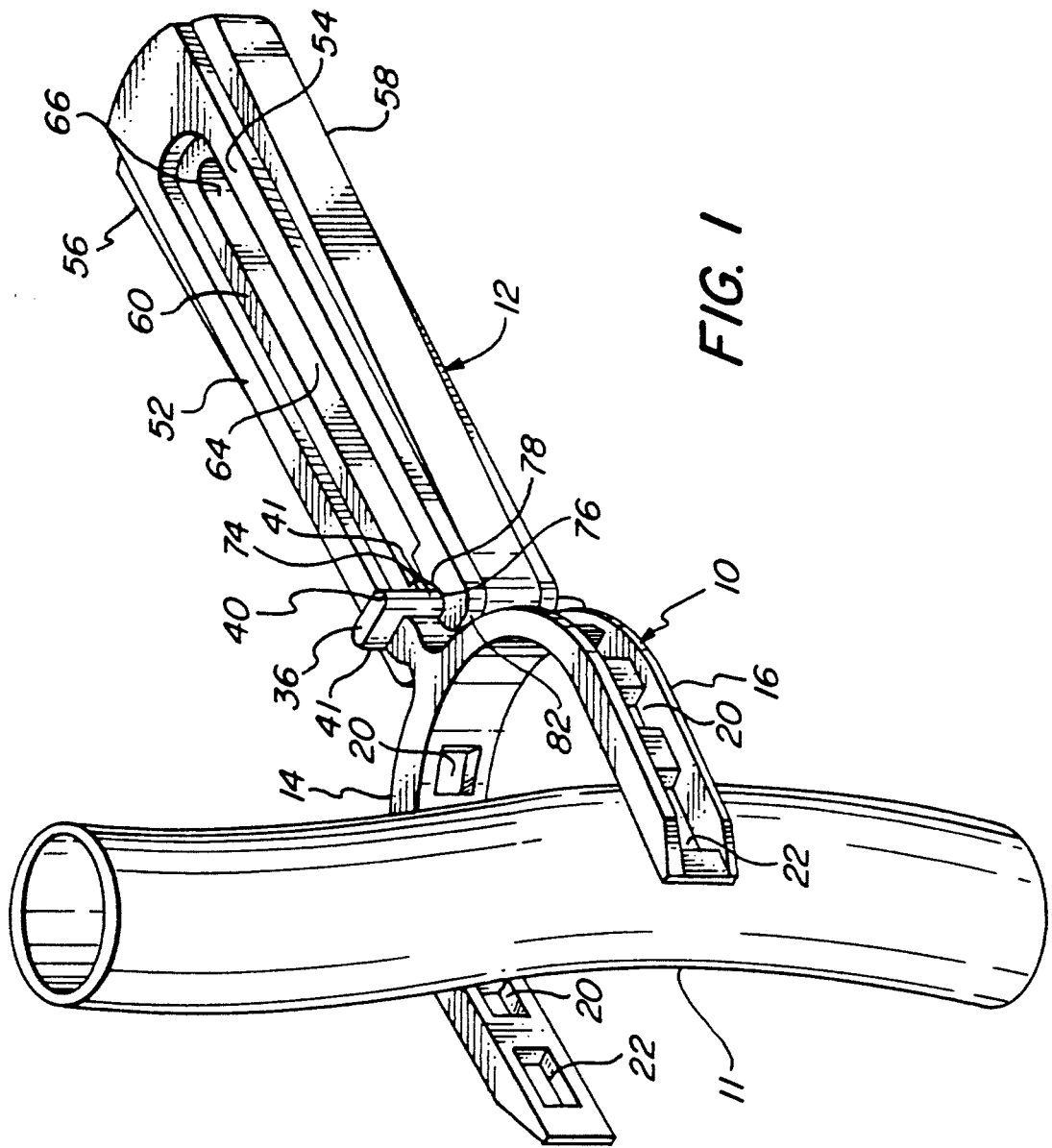
FIGS. 1 to 3 are perspective views of the surgical ligation clip showing how it is positioned around the blood vessel to be ligated during different stages of use in accordance with the present invention.
Figure 3:
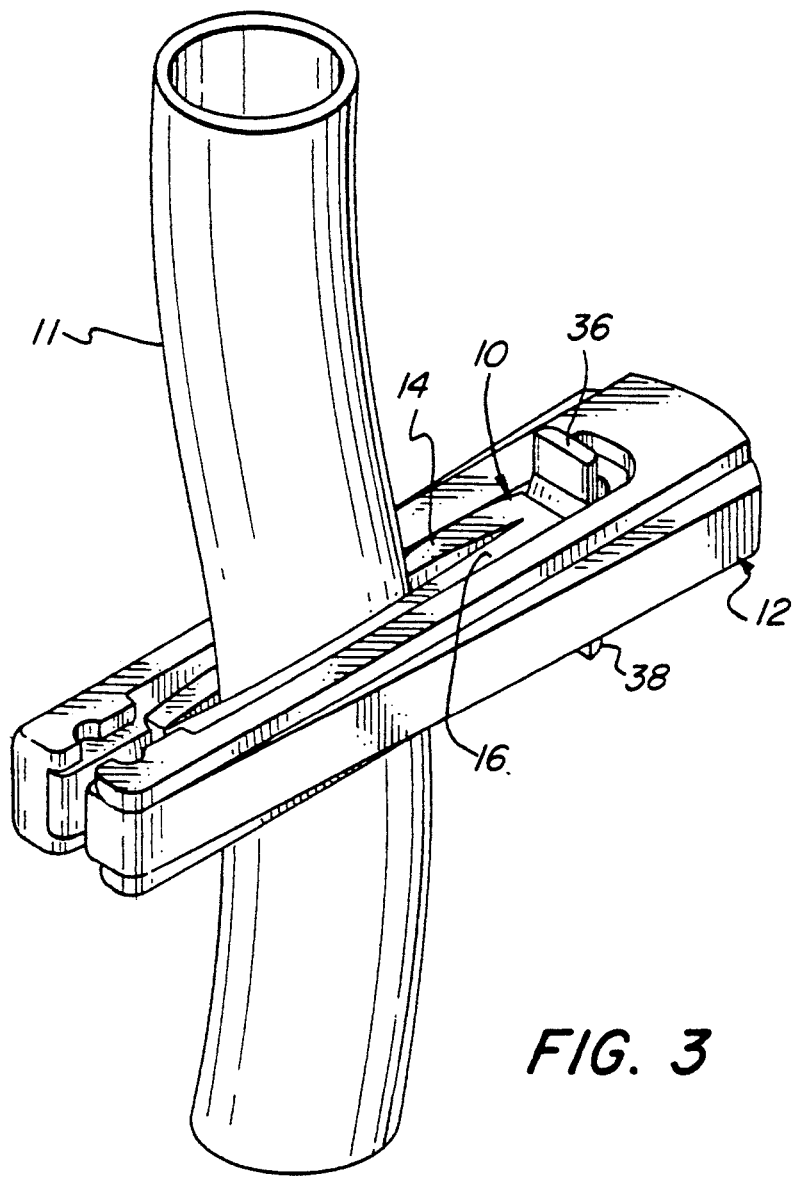

FIG. 1 shows a preferred embodiment of the surgical ligation clip of the subject invention. The two main components of the ligation clip are a track 10 and a clip 12, which are preferably made of a non-metallic resilient polymer-type material. The track is relatively flexible while the clip is made of a relatively rigid material. Generally speaking, the track is connected to the clip and positioned around, for example, a blood vessel 11 to be ligated. The track is held stationary and the clip is forced forwardly so the track and clip slide relative to each other. This sliding motion closes and locks the track about the blood vessel as shown in FIG. 3.

The track 10 will be discussed in detail with reference to FIGS. 4 through 7. The track is comprised of two curved arms 14 and 16 positioned to form a C-shaped clamp. The arms are connected at their proximal ends at apex 18. The distal ends of the arms form tips 24 and 26 which are spaced apart from each other in substantially parallel relationship for receiving the blood vessel.

Figure 6:
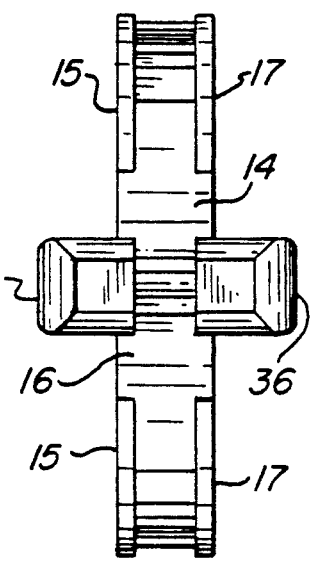
FIG. 6 is an end elevational view of the track in accordance with the present invention.
Figure 5:
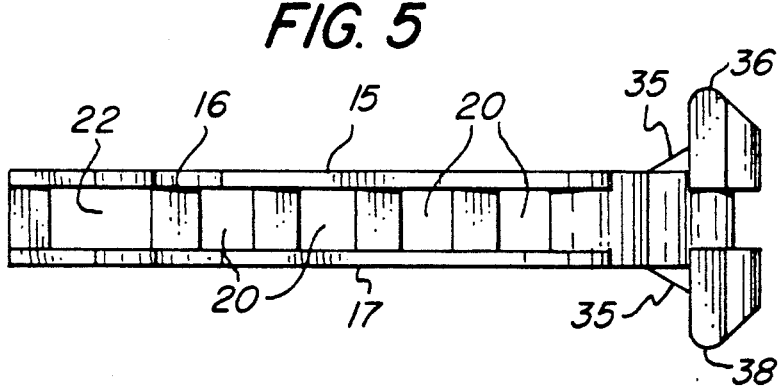
FIG. 5 is a side elevational view of the track in accordance with the present invention.

As best shown in FIGS. 5 and 6, each arm is strengthened by upper and lower ribs 15 and 17. In addition, the arms are formed with a series of windows along their axial direction. A plurality of small windows 20 are spaced in the middle portion of each arm, and a single large window 22 is spaced toward the distal tip of each arm. The windows provide a series of ridges and openings for improved gripping of the blood vessel. The large windows also provide means to lock the track in a closed position as will be described below.

Figure 4:
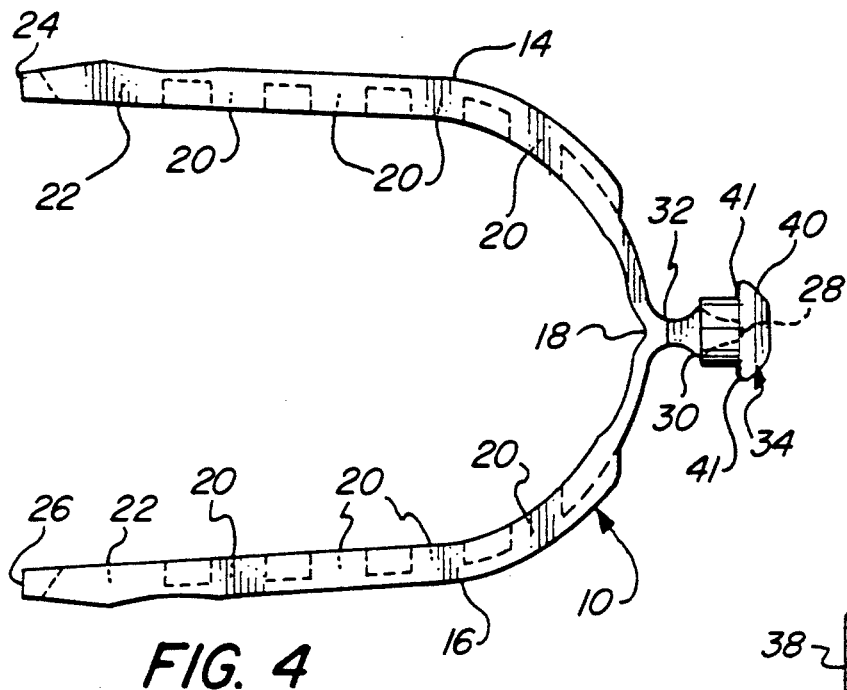
FIG. 4 is a top plan view of the track in accordance with the present invention.
Figure 7:
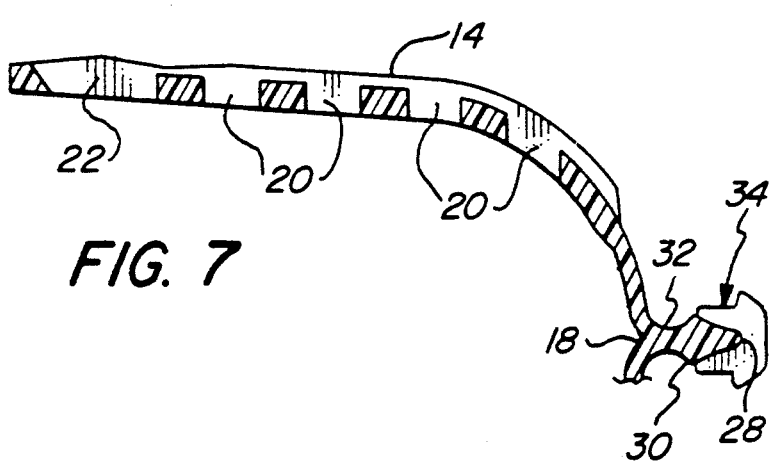
FIG. 7 is a partial top plan view, partially in cross-section, of the track in accordance with the present invention.

The apex of the track is shaped, as shown in FIGS. 4 and 7, to have a protruding rib 28, a bulbous portion 30 and a neck 32. A connector 34 is secured on the apex, for connecting the track to the clip. As shown in FIG. 5, reinforcing ribs 35 assist in securing the connector to the apex. The connector is shown in FIGS. 5 and 6 to have two posts 36 and 38 extending in opposite directions. With reference to FIG. 4, the posts are shown as being "T"-shaped in cross-section, and having chamfered edges 40 and protrusions 41.

Figure 8:
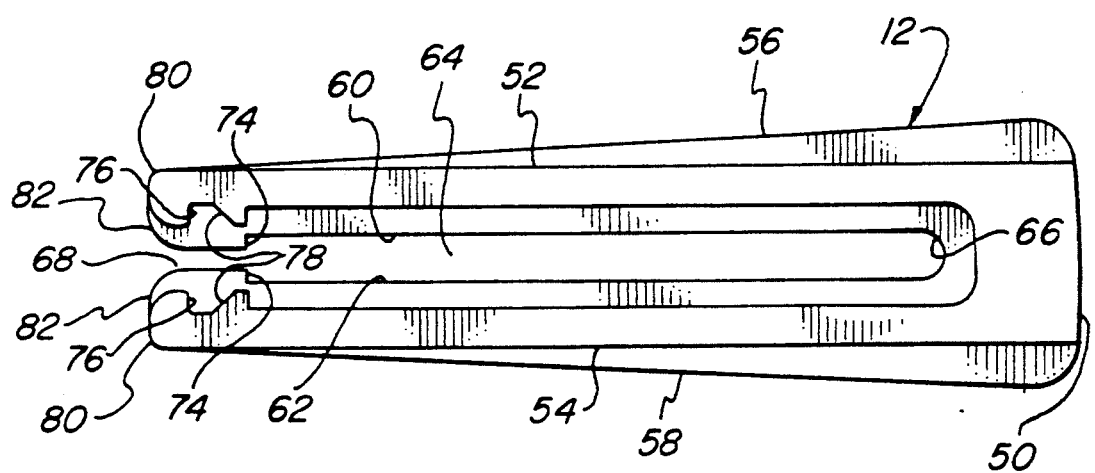
FIG. 8 is a top plan view of the clip in accordance with the present invention.

The clip 12 will be described in detail with reference to FIGS. 1 and 8. It is comprised generally of a U-shaped body 50 formed of cantilevered limbs 52 and 54. Tapered ribs 56 and 58 on an outside surface of the limbs provide strength, and interior ribs 60 and 62 define an extended slot 64 which extends from a crotch section 66 of the body at its proximal end to opening 68 at its distal end.

Distal ends of interior ribs 60 and 62 are shaped to form a key 74, or first contour surface. Each cantilevered limb 52 and 54 has a second contour surface formed of a notch 76 and chamfered surface 78, or second contour surface, for engaging with complementary surfaces on the track. Distal tips 80 of the cantilevred limbs are shaped to have radial camming surfaces 82 for engaging the track in a manner described below.

When track 10 is connected to clip 12 as shown in FIG. 1, the track is locked in the open position by virtue of the engagement between posts 36 and 38 of the track and the cantilevered limbs of the clip. More particularly, protruding portions 41 of the posts fit into notches 76 in the cantilevered limbs. In addition, chamfered edges 40 of the posts face the complementary chamfered surfaces 78 of the cantilevered limbs. At this position the track cannot be easily removed from the clip unless, for example, the cantilevered limbs are urged outwardly a substantial distance so the notches clear the protruding portions of the track. Thus, the chances of accidental disconnection of the track from the clip are relatively small.

Figure 2:
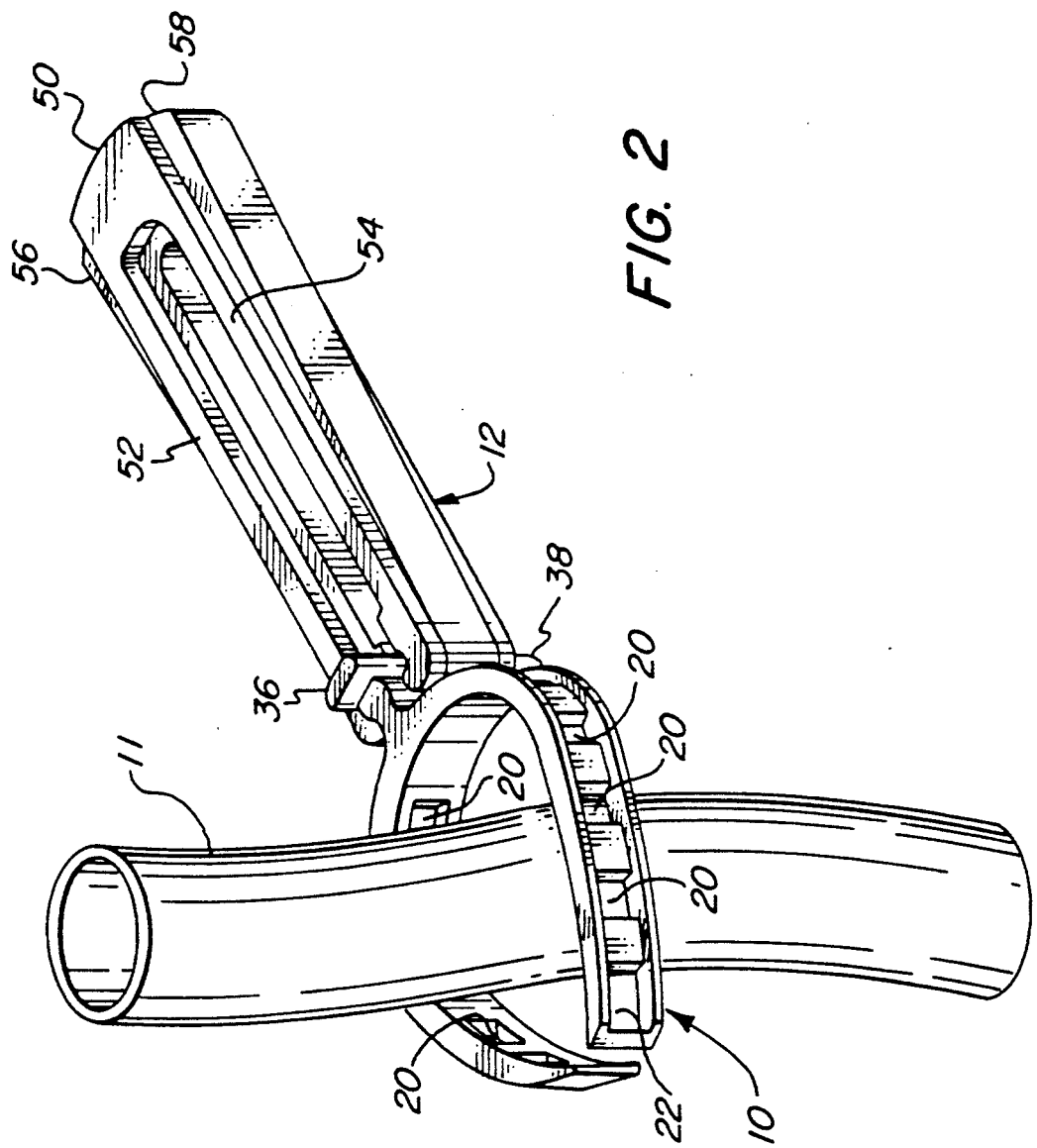

To close the ligation clip around the blood vessel, the track is held stationary by gripping posts 36 and 38 and the clip is slid forwardly toward the track. This sliding action urges the cantilevered limbs slightly outwardly and releases protruding portions 41 from notches 76 as the complementary chamfered edges 40 and chamfered surfaces 78 slide relative to each other. The sliding action also urges camming surfaces 82 of the cantilevered limbs against the curved arms 14 and 16 and begins to close the C-shaped clamp as shown in FIG. 2.

The ligation clip is shown in the closed position in FIG. 3. As will be appreciated, the closed position is achieved when the track completely occupies the elongated slot 64, with the posts 36 and 38 positioned at the proximal end of the clip. The ligation clip is locked in the closed position by engagement of keys 74 of the inner ribs in the large windows in the arms. Since the keys are shaped to be larger than the small windows, the ligation clip will only lock when the keys are registered with the large windows. Thus in the locked position of the clip, the blood vessel is securely ligated.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

I claim:

1. A two-part surgical ligation clip, comprising:

a track including two substantially symmetrical arms connected together at a proximal end to form an apex and having spaced tips at a distal end with first complementary surfaces, said track also including a connector to said apex and having a second complementary surface; and a clip having an extended slot for slidably engaging said track and distal end tips for receiving said connector, with a distal end of said clip having a first contour surface and a second contour surface, wherein said first contour surface engages and interlocks with said first complementary surfaces on said track to lock said track in a closed position, said second contour surface engages and interlocks with said second complementary surface on said track to lock said track in an open position.

2. A two-part surgical ligation clip according to claim 1, wherein said first complementary surfaces comprise a large window disposed at the distal end of each said arm and said first contour surface comprises a pair of keys oppositely disposed at an interior surface of said clip, with each said key interlocking with one of said large windows to lock said track in a closed position.

3. A two-part surgical ligation clip according to claim 1, wherein said connector includes two posts extending in opposite directions, with said posts having a substantially T-shaped cross-section and chamfered edges to form said second complementary surface, and said second contour surface comprises a notched portion contiguous with a chamfered surface at an interior surface of said clip.

4. A two-part surgical ligation clip comprising:

a track including two substantially symmetrical arms connected together at a proximal end to form an apex and having spaced tips at a distal end with first complementary surfaces, said track also including a connector connected to said apex and having a second complementary surface; and a clip having an extended slot for slidably engaging said track and distal end tips for receiving said connector, with a distal end of said clip having a first contour surface for engaging said first complementary surfaces on said track and locking said track in a closed position and a second contour surface for engaging said second complementary surface on said track and locking said track in an open position, wherein said first complementary surfaces comprise a large window disposed at the distal end of each said arm, and said connector includes two posts extending in opposite directions, with said posts having a substantially T-shaped cross-section and chamfered edges to form said second complementary surfaces.

5. A two-part surgical ligation clip according to claim 4, wherein said first contour surface comprises a pair of keys oppositely disposed at an interior surface of said clip.

6. A two-part surgical ligation clip according to claim 5, wherein said second contour surface comprises a notched portion contiguous with a chamfered surface at said interior surface of said clip.

7. A two-part surgical ligation clip according to claim 6, wherein said clip is formed by two cantilevered limbs connected at a proximal end to form a substantially U-shaped clip.

8. A two-part surgical ligation clip according to claim 7, wherein each said limb includes an interior rib for defining the extended slot, with said keys being disposed at an interior surface of said interior ribs.

9. A two-part surgical ligation clip according to claim 8, wherein said distal end tips include radially curved exterior surfaces for camming said arms as said track and said clip slide relative to each other.

10. A two-part surgical ligation clip according to claim 9, further comprising tapered ribs disposed on an exterior surface of said limbs.

11. A two part surgical ligation clip according to claim 10, wherein said arms are curved and together form a substantially C-shaped track in the open position.

12. A two-part surgical ligation clip according to claim 11, wherein each said arm includes a plurality of windows extending along its axial direction.

13. A two-part surgical ligation clip according to claim 12, wherein said plurality of windows includes a series of small windows and a single large window at the distal end of each said arm.

14. A surgical ligation clip, comprising:
a track having two arms for engaging around a vessel to be ligated, said arms being joined together at a proximal end of said track;
a clip having an extended slot for slidably receiving said track;
first interlocking means, located at distal ends of said track and said clip, for engaging and interlocking said track in a closed position in said clip; and
second interlocking means, located at the distal end of said clip and the proximal end of said track, for engaging and interlocking said track in an open position in said clip.

15. A surgical ligation clip according to claim 14, wherein said first interlocking means includes a first complementary surface at a distal each said arm and a first contour surface at the distal end of said clip.

16. A surgical ligation clip according to claim 15, wherein said first complementary surface is formed by large windows disposed at the distal ends of said arms, and further comprising a pair of keys forming said first contour surface at the distal end of said clip.

17. A surgical ligation clip according to claim 14, wherein said second interlocking means includes a connector, connected to the proximal end of said track, having a second complementary surface, and a second contour surface located at the distal end of said clip.

18. A surgical ligation clip according to claim 17, wherein said connector comprises two posts each having a substantially T-shaped cross-section and chamfered edges to form said second complementary surface, and said second contour surface is formed by a notched portion contiguous with a chamfered surface at the distal end of said clip.

19. A surgical ligation clip, comprising:
a track having two arms for engaging around a vessel to be ligated, said arms being joined together at a proximal end of said track;
a clip having an extended slot for slidably receiving said track;
first locking means, located at distal ends of said track and said clip, for locking said track in a closed position in said clip; and
second locking means, located at the distal end of said clip and the proximal end of said track, for locking said track in an open position in said clip, wherein
said first locking means includes a first complementary surface at the distal end of each said arm and a first contour surface at the distal end of said clip, said second locking means includes a connector, connected to the proximal end of said track, having a second complementary surface, and a second contour surface located at the distal end of said clip, and
wherein said first complementary surface is formed by large windows disposed at distal ends of said arms, and further comprising a pair of keys forming said first contour surface the distal end of said clip, and said connector comprises two posts each having a substantially T-shaped cross-section and chamfered edges to form said second complementary surface, and said second contour surface is formed by a notched portion contiguous with a chamfered surface at the distal end of said clip.

20. A surgical ligation clip according to claim 19, wherein said arms are curved and together form a substantially C-shaped track in the open position.

21. A surgical ligation clip according to claim 20, wherein each arm includes a plurality of windows extending along its axial direction, and said plurality of windows includes a series of small windows and a single large window at the distal end of each said arm.

22. A surgical ligation clip according to claim 21, wherein said clip is formed by two cantilevered limbs connected at a proximal end to form a substantially U-shaped clip.

23. A surgical ligation clip according to claim 22, wherein said notched portion and chamfered surface are formed on distal ends of said cantilevered limbs.

24. A surgical ligation clip according to claim 23, further comprising interior ribs formed on said cantilevered limbs, wherein said keys are formed on distal ends of said interior ribs.

25. A two-part surgical ligation clip, comprising:
a track including two substantially symmetrical arms connected together at a proximal end to form an apex and having spaced tips at a distal end, said track also including a connector connected to said apex and formed with a first complementary surface; and
a clip having an extended slot for slidably engaging said track and distal end tips for receiving said connector, with a distal end of said clip having a first contour surface, wherein
said first contour surface is formed to receive said first complementary surface on said track and thereby to lock said track in an open position, and one of said first complementary surface and said first contour surface comprises a notch and the other of said first complementary surface and said first contour surface comprises post means formed to be received in said notch, thereby to lock said track in an open position relative to said clip.

26. A two-part surgical ligation clip according to claim 25, wherein said notch comprises said first contour surface and is formed in the region of the one of said distal end tips.

27. A two-part surgical ligation clip according to claim 26, wherein said post means comprises said first complementary surface and is formed on said connector of said track.

28. A two-part surgical ligation clip, comprising:
a track including two substantially symmetrical arms connected together at a proximal end to form an apex and having spaced tips at a distal end, said track also including a connector connected to said apex and a first complementary surface formed at at least one distal end of at least one said arm; and
a clip having an extended slot for slidably engaging said track and distal end tips for receiving said connector, with a distal end of said clip having a first contour surface, wherein
said first contour surface is formed to interlock with said first complementary surface on said track and thereby to lock said track in a closed position, and one of said first complementary surface and said first contour surface comprises a notch and the other of said first complementary surface and said first contour surface comprises means formed to be received in said notch, thereby to lock said track in a closed position relative to said clip.

29. A two-part surgical ligation clip according to claim 28, wherein said notch comprises said first complementary surface and is formed in the region of at least one of said distal ends of at least one said arm.

30. A two-part surgical ligation clip according to claim 28, wherein said means formed to be received in said notch comprises said first contour surface and is formed on at least one said distal end tip of said clip.

* * * * *

UNITED STATES PATENT AND TRADEMARK OFFICE
CERTIFICATE OF CORRECTION

PATENT NO. : 5,306,283

DATED : April 26, 1994

INVENTOR(S) : John A. Connors

It is certified that error appears in the above-indentified patent and that said Letters Patent is hereby corrected as shown below:

Column 5, line 3, claim 15, after "distal" insert --end of--.

Signed and Sealed this

Thirteenth Day of September, 1994

Attest:

BRUCE LEHMAN

Attesting Officer          Commissioner of Patents and Trademarks